United States Patent [19]
Oetjen

[11] Patent Number: 5,562,647
[45] Date of Patent: Oct. 8, 1996

[54] SANITARY NAPKIN HAVING A FLUID PERVIOUS PERIPHERAL MASKING MEMBER

[75] Inventor: Wendy Oetjen, West Chester, Ohio

[73] Assignee: The Procter & Gamble Company, Cincinnati, Ohio

[21] Appl. No.: 243,021

[22] Filed: May 16, 1994

[51] Int. Cl.⁶ .............................. A61F 13/15; A61F 13/20
[52] U.S. Cl. ..................... 604/370; 604/378; 604/385.1
[58] Field of Search .................................. 604/358–362, 604/378, 385.1, 370

[56] References Cited

U.S. PATENT DOCUMENTS

| | | | |
|---|---|---|---|
| 1,946,626 | 2/1934 | Jurgensen | 604/358 |
| 2,721,554 | 10/1955 | Joa . | |
| 2,896,627 | 7/1959 | Harwood | 604/370 |
| 3,888,254 | 6/1975 | Hendricks | 604/370 |
| 4,014,341 | 3/1977 | Karami . | |
| 4,333,465 | 6/1982 | Wiegner | 604/358 |
| 4,781,962 | 11/1988 | Zamarripa et al. . | |
| 4,900,318 | 2/1990 | Toth . | |
| 5,176,672 | 1/1993 | Bruemmer et al. | 604/385.1 |
| 5,188,626 | 2/1993 | Toyoda et al. | 604/385.1 |
| 5,219,341 | 6/1993 | Serbiak et al. | 604/361 |
| 5,261,899 | 11/1993 | Visscher et al. | 604/367 |
| 5,415,640 | 5/1995 | Kirby et al. | 604/383 |

FOREIGN PATENT DOCUMENTS

| | | |
|---|---|---|
| 0176914 | 4/1986 | European Pat. Off. . |
| 0543116A1 | 5/1993 | European Pat. Off. . |
| 338553 | 7/1959 | Switzerland . |
| 430269 | 7/1935 | United Kingdom . |

*Primary Examiner*—John G. Weiss
*Assistant Examiner*—P. Zuttarelli
*Attorney, Agent, or Firm*—Kevin C. Johnson; William Scott Andes; E. Kelly Linman

[57] ABSTRACT

A sanitary napkin having a periphery and including a fluid pervious topsheet, a fluid impervious backsheet joined to said topsheet and an absorbent core having a periphery positioned between said topsheet and said backsheet. The sanitary napkin also includes a fluid pervious masking member positioned between the topsheet and the absorbent core. The masking member is disposed along the periphery of the sanitary napkin and covers the periphery of the absorbent core.

6 Claims, 2 Drawing Sheets

SANITARY NAPKIN HAVING A FLUID PERVIOUS PERIPHERAL MASKING MEMBER

TECHNICAL FIELD

The present invention relates to absorbent articles such as sanitary napkins, pantiliners, incontinence pads, and the like. More particularly, the present invention relates to sanitary napkins having a fluid pervious peripheral masking member.

BACKGROUND OF THE INVENTION

Sanitary napkins configured for the absorption of bodily fluids are, of course, well-known. In their simplest form they comprise an absorbent element or core interposed between a liquid pervious body contacting element and a liquid impervious protective barrier. The absorbent element (sometimes called the absorbent core) is, of course, intended to receive and contain menses and other vaginal discharges. The body contacting element (sometimes called a topsheet) is intended to provide more or less confortable and dry-feeling contact with body surfaces while allowing free passage of fluids therethrough and into the absorbent core. The protective barrier (sometimes called the backsheet) is intended to prevent menses or other vaginal discharges which are expelled or escape from the absorbent core from soiling the user's undergarments.

Recently, improvements in the absorbent core have increased their overall absorptive capacity, To increase the absorptive capacity of absorbent cores, improvements have been made in their ability to wick fluid. As fluid enters the absorbent core it is preferably able to wick in all directions to the peripheral edges of the absorbent core. While an increase in the overall absorptive capacity has proved to be beneficial in the prevention of soiling of undergarments and the like, the visual impression to tile user is that the absorbent core has reached its capacity and is near failure due to the presence of bodily fluids adjacent to or in the peripheral zones of the absorbent core. However, in most instances this is not the case as the absorbent core is able to hold more fluid before reaching its capacity.

SUMMARY OF THE INVENTION

The present invention provides an absorbent article, such as a sanitary napkin. More particularly, the present invention provides a sanitary napkin having a periphery. The sanitary napkin comprises a fluid pervious topsheet and a fluid impervious backsheet joined to the topsheet. The topsheet may be made from a wide range of materials including nonwoven materials and apertured formed films. An absorbent core having a periphery is positioned between the topsheet and the backsheet. A fluid pervious masking member is positioned between said topsheet and said absorbent core. The masking member is disposed along the periphery of said sanitary napkin to define a centrally disposed open area. Preferably, the masking member is positioned such that it covers the periphery of the absorbent core. The masking member may be made from a wide range of materials including nonwoven materials and apertured formed films.

In a preferred embodiment the topsheet, the backsheet, and the masking member are secured together along their common periphery.

BRIEF DESCRIPTION OF THE DRAWINGS

While the specification concludes with claims particularly pointing out and distinctly claiming the present invention, it is believed that the present invention will be better understood from the following description in conjunction with the accompanying drawings in which like reference numbers identify identical elements and wherein:

DETAILED DESCRIPTION OF THE INVENTION

As used herein, the term "absorbent article" refers to devices which absorb and contain body exudates, and, more specifically, refers to devices which are placed against or in proximity to the body of the wearer to absorb and contain the various exudates discharged from the body. The term "disposable" is used herein to describe absorbent articles which are not intended to be laundered or otherwise restored or reused as an absorbent article (i.e., they are intended to be discarded after a single use, and, preferably, to be recycled, composted or otherwise disposed of in an environmentally compatible manner). A "unitary" absorbent article refers to absorbent articles which are formed of separate parts united together to form a coordinated entity so that they do not require separate manipulative parts like a separate holder and pad.

Figure 1:
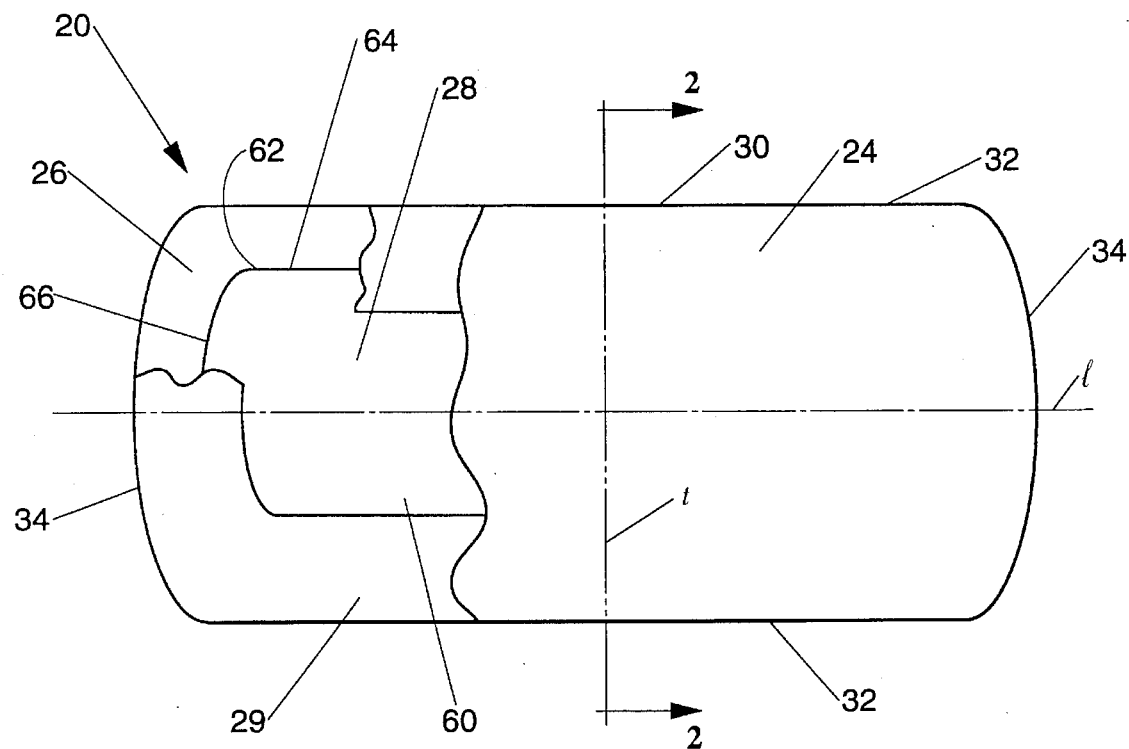
FIG. 1 is a top plan view of a sanitary napkin embodiment of the present invention with portions of the sanitary napkin cut-away to more clearly show the construction of the sanitary napkin.

A preferred embodiment of a unitary disposable absorbent article of the present invention is the catamenial pad, sanitary napkin 20, shown in FIG. 1. As used herein, the term "sanitary napkin" refers to an absorbent article which is worn by females adjacent to the pudendal region, generally external to the urogenital region, and which is intended to absorb and contain menstrual fluids and other vaginal discharges from the wearer's body (e.g., blood, menses, and urine). Interlabial devices which reside partially within and partially external of the wearer's vestibule are also within the scope of this invention. As used herein, the term "pudendal" refers to the externally visible female genitalia. It should be understood, however, that the present invention is also applicable to other feminine hygiene or catamenial pads such as pantiliners, or other absorbent articles such as incontinence pads, and the like.

FIG. 1 is a top plan view of the sanitary napkin 20 of the present invention in its flat-out state with portions of the structure being cut-away to more clearly show the construction of the sanitary napkin 20 and with the portion of the sanitary napkin 20 which faces or contacts the wearer, oriented towards the viewer. As shown in FIG. 1, the sanitary napkin 20 preferably comprises a liquid pervious topsheet 24, a liquid impervious backsheet 26 joined with the topsheet 24, an absorbent core 28 positioned between the topsheet 24 and the backsheet 26, and a fluid pervious masking member 29 positioned between the topsheet 24 and the absorbent core 28 and adjacent the periphery 30 of the sanitary napkin.

The sanitary napkin 20 has two surfaces, a body-contacting surface or "body surface" and a garment surface. The sanitary napkin 20 is shown in FIG. 1 as viewed from its body surface. The body surface is intended to be worn adjacent to the body of the wearer while the garment surface is on the opposite side and is intended to be placed adjacent to the wearer's undergarments when the sanitary napkin 20 is worn.

The sanitary napkin 20 has two centerlines, a longitudinal centerline "l" and a transverse centerline "t". The term "longitudinal", as used herein, refers to a line, axis or direction in the plane of the sanitary napkin 20 that is generally aligned with (e.g., approximately parallel to) a vertical plane which bisects a standing wearer into left and right body halves when the sanitary napkin 20 is worn. The terms "transverse" or "lateral" as used herein, are interchangeable, and refer to a line, axis or direction which lies within the plane of the sanitary napkin 20 that is generally perpendicular to the longitudinal direction.

FIG. 1 also shows that the sanitary napkin 20 has a periphery 30 which is defined by the outer edges of the sanitary napkin 20 in which the longitudinal edges are designated 32 and the end edges are designated 34.

Figure 2:
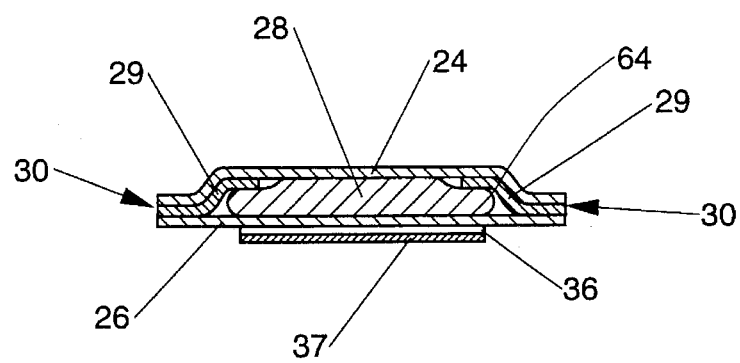
FIG. 2 is a cross-sectional view of the sanitary napkin of FIG. 1 taken along section line 2—2.

FIG. 2 is a cross-sectional view of the sanitary napkin 20 taken along section line 2—2 of FIG. 1. As can be seen in FIG. 2, the sanitary napkin 20 preferably includes an adhesive fastening means 36 for attaching the sanitary napkin 20 to the undergarment of the wearer. Removable release liners 37 cover the adhesive fastening means 36 to keep the adhesive from sticking to a surface other than the crotch portion of the undergarment prior to use.

While the topsheet, the backsheet, and the absorbent core may be assembled in a variety of well known configurations (including so called "tube" products or side flap products), preferred sanitary napkin configurations are described generally in U.S. Pat. No. 4,950,264, issued to Osborn on Aug. 21, 1990; U.S. Pat. No. 4,425,130, issued to DesMarais on Jan. 10, 1984; U.S. Pat. No. 4,321,924, issued to Ahr on Mar. 30, 1982: and U.S. Pat. No. 4,589,876, issued to Van Tilburg on Aug. 18, 1987. Each of these patents are hereby incorporated herein by reference. FIG. 1 shows a preferred embodiment of the sanitary napkin 20 in which the topsheet 24 and the backsheet 26 have length and width dimensions generally larger than those of the absorbent core 28. The topsheet 24 and the backsheet 26 extend beyond the edges of the absorbent core 28 to thereby form a portion of the periphery of the sanitary napkin.

The absorbent core 28 may be any absorbent means which is capable of absorbing or retaining liquids (e.g., menses and/or urine). As shown in FIG. 1, the absorbent core 28 has a body surface, a garment surface, and a periphery 62. Periphery 62 is defined by the outer edges of the absorbent core 28 in which longitudinal edges are designated 64 and the end edges are designated 66. The absorbent core 28 may be manufactured in a wide variety of sizes and shapes (e.g., rectangular, oval, hourglass, dog bone, asymmetric, etc.) and from a wide variety of liquid-absorbent materials commonly used in sanitary napkins and other absorbent articles such as comminuted wood pulp which is generally referred to as airfelt. Examples of other suitable absorbent materials include creped cellulose wadding; meltblown polymers including coform; chemically stiffened, modified or cross-linked cellulosic fibers; synthetic fibers such as crimped polyester fibers; peat moss; tissue including tissue wraps and tissue laminates; absorbent foams; absorbent sponges; superabsorbent polymers; absorbent gelling materials; or any equivalent material or combinations of materials, or mixtures of these. The configuration and construction of the absorbent core may also be varied (e.g., the absorbent core may have varying caliper zones (e.g., profiled so as to be thicker in the center), hydrophilic gradients, superabsorbent gradients, or lower density and lower average basis weight acquisition zones; or may comprise one or more layers or structures). The total absorbent capacity of the absorbent core should, however, be compatible with the design loading and the intended use of the sanitary napkin. Further, the size and absorbent capacity of the absorbent core may be varied to accommodate different uses such as incontinence pads, pantiliners, regular sanitary napkins, or overnight sanitary napkins.

Exemplary absorbent structures for use as the absorbent core of the present invention are described in U.S. Pat. No. 4,950,264, issued to Osborn on Aug. 21, 1990; U.S. Pat. No. 4,610,678, issued to Weisman et al. on Sep. 9, 1986; U.S. Pat. No. 4,834,735, issued to Alemany et al. on May 30, 1989; and European Patent Application No. 0 198 683, The Procter & Gamble Company, published Oct. 22, 1986 in the name of Duenk, et al. Each of these patents are incorporated herein by reference.

The backsheet 26 and the topsheet 24 are positioned adjacent the garment surface and the body surface, respectively, of the absorbent core 28 and are preferably joined thereto and to the masking member 29 or each other by attachment means (not shown) such as those well known in the art. For example, the backsheet 26 and/or the topsheet 24 may be secured to the absorbent core 28, the masking member 29, or to each other by a uniform continuous layer of adhesive, a patterned layer of adhesive, or an array of separate lines, spirals, or spots of adhesive. Adhesives which have been found to be satisfactory are manufactured by H. B. Fuller Company of St. Paul, Minn. under the designation HL-1258 or H-2031. The attachment means will preferably comprise an open pattern network of filaments of adhesive as is disclosed in U.S. Pat. No. 4,573,986, issued to Minetola, et al. on Mar. 4, 1986, and which is incorporated herein by reference. An exemplary attachment means of an open pattern network of filaments comprises several lines of adhesive filaments swirled into a spiral pattern such as illustrated by the apparatus and method shown in U.S. Pat. No. 3,911,173, issued to Sprague, Jr. on Oct. 7, 1975; U.S. Pat. No. 4,785,996, issued to Zieker, et al. on Nov. 22, 1978; and U.S. Pat. No. 4,842,666 issued to Werenicz on Jun. 27, 1989. Each of these patents are incorporated herein by reference. Alternatively, the attachment means may comprise heat bonds, pressure bonds, ultrasonic bonds, dynamic mechanical bonds, or any other suitable attachment means or combinations of these attachment means as are known in the art.

The backsheet 26 is impervious to liquids (e.g., menses and/or urine) and is preferably manufactured from a thin plastic film, although other flexible liquid impervious materials may also be used. As used herein, the term "flexible" refers to materials which are compliant and will readily conform to the general shape and contours of the human body. The backsheet 26 prevents the exudates absorbed and contained in the absorbent core 28 from wetting articles which contact the sanitary napkin 20 such as pants, pajamas and undergarments. The backsheet 26 may thus comprise a woven or nonwoven material, polymeric films such as thermoplastic films of polyethylene or polypropylene, or composite materials such as a film-coated nonwoven material. Preferably, the backsheet is a polyethylene film having a thickness of from about 0.012 mm (0.5 mil) to about 0.051 mm (2.0 mils). Exemplary polyethylene films are manufactured by Clopay Corporation of Cincinnati, Ohio, under the designation P18-0401 and by Ethyl Corporation, Visqueen Division, of Terre Haute, Ind., under the designation XP-39385. The backsheet is preferably embossed and/or matte finished to provide a more clothlike appearance. Further, the backsheet 26 may permit vapors to escape from the absorbent core 28 (i.e., breathable) while still preventing exudates from passing through the backsheet 26.

The topsheet 24 is compliant, soft feeling, and non-irritating to the wearer's skin. Further, the topsheet 24 is liquid pervious permitting liquids (e.g., menses and/or urine) to readily penetrate through its thickness. A suitable topsheet 24 may be manufactured from a wide range of materials such as woven and nonwoven materials; polymeric materials such as apertured formed thermoplastic films, apertured plastic films, and hydroformed thermoplastic films; porous foams; reticulated foams; reticulated thermoplastic films; and thermoplastic scrims. Suitable woven and nonwoven materials can be comprised of natural fibers (e.g., wood or cotton fibers), synthetic fibers (e.g., polymeric fibers such as polyester, polypropylene, or polyethylene fibers) or from a combination of natural and synthetic fibers. A preferred topsheet comprises an apertured formed film. Apertured formed films are preferred for the topsheet because they are pervious to body exudates and yet non-absorbent and have a reduced tendency to allow liquids to pass back through and rewet the wearer's skin. Thus, the surface of the formed film which is in contact with the body remains dry, thereby reducing body soiling and creating a more comfortable feel for the wearer. Suitable formed films are described in U.S. Pat. No. 3,929,135, issued to Thompson on Dec. 30, 1975; U.S. Pat. No. 4,324,246, issued to Mullane, et al. on Apr. 13, 1982; U.S. Pat. No. 4,342,314, issued to Radel. et al. on Aug. 3, 1982; U.S. Pat. No. 4,463,045, issued to Ahr et al. on Jul. 31, 1984; and U.S. Pat. No. 5,006,394, issued to Baird on Apr. 9, 1991. Each of these patents are incorporated herein by reference. The preferred topsheet for the present invention is the formed film described in one or more of the above patents and marketed on sanitary napkins by The Procter & Gamble Company of Cincinnati, Ohio as "DRI-WEAVE".

In a preferred embodiment of the present invention, the body surface of the formed film topsheet is hydrophilic so as to help liquid to transfer through the topsheet faster than if the body surface was not hydrophilic so as to diminish the likelihood that menstrual fluid will flow off the topsheet rather than flowing into and being absorbed by the absorbent core. In a preferred embodiment, surfactant is incorporated into the polymeric materials of the formed film topsheet such as is described in U.S. Patent Application Ser. No. 07/794,745, "Absorbent Article Having A Nonwoven and Apertured Film Coversheet" filed on Nov. 19, 1991 by Aziz, et al., which is incorporated herein by reference. Alternatively, the body surface of the topsheet can be made hydrophilic by treating it with a surfactant such as is described in the above referenced U.S. Pat. No. 4,950,254 issued to Osborn, incorporated herein by reference.

The fluid pervious masking member 29 is positioned between the topsheet 24 and the backsheet 26 and preferably forms a portion of the periphery 30 of the sanitary napkin 20. The masking member 29 is preferably positioned on the body surface of the absorbent core 28 and covers the periphery 62 of the absorbent core 28. A suitable masking member 29 may be manufactured from a wide range of materials such as woven and nonwoven materials; polymeric material such as apertured formed thermoplastic films, apertured plastic films, and hydroformed thermoplastic films; porous foams, reticulated foams; reticulated thermoplastic films; and thermoplastic scrims. Suitable woven and nonwoven materials can be comprised of natural fibers (e.g., wood or cotton fibers), synthetic fibers (e.g., polymeric fibers such as polyester, polypropylene, or polyethylene fibers) or from a combination of natural and synthetic fibers. A preferred masking member comprises an apertured formed film. Apertured formed films are preferred for the masking member 29 because they are pervious to body exudates and yet non-absorbent and have a reduced tendency to allow liquids to pass back through toward the wearer's skin. Suitable formed films are described in the above-referenced U.S. Pat. Nos. 3,929,135, issued to Thompson; 4,324,246, issued to Mullane, et at; 4,342,314, issued to Radel, et at; 4,463,045, issued to Ahr, et al; and 5,006,394, issued to Baird, each of which is incorporated herein by reference.

Figure 3:
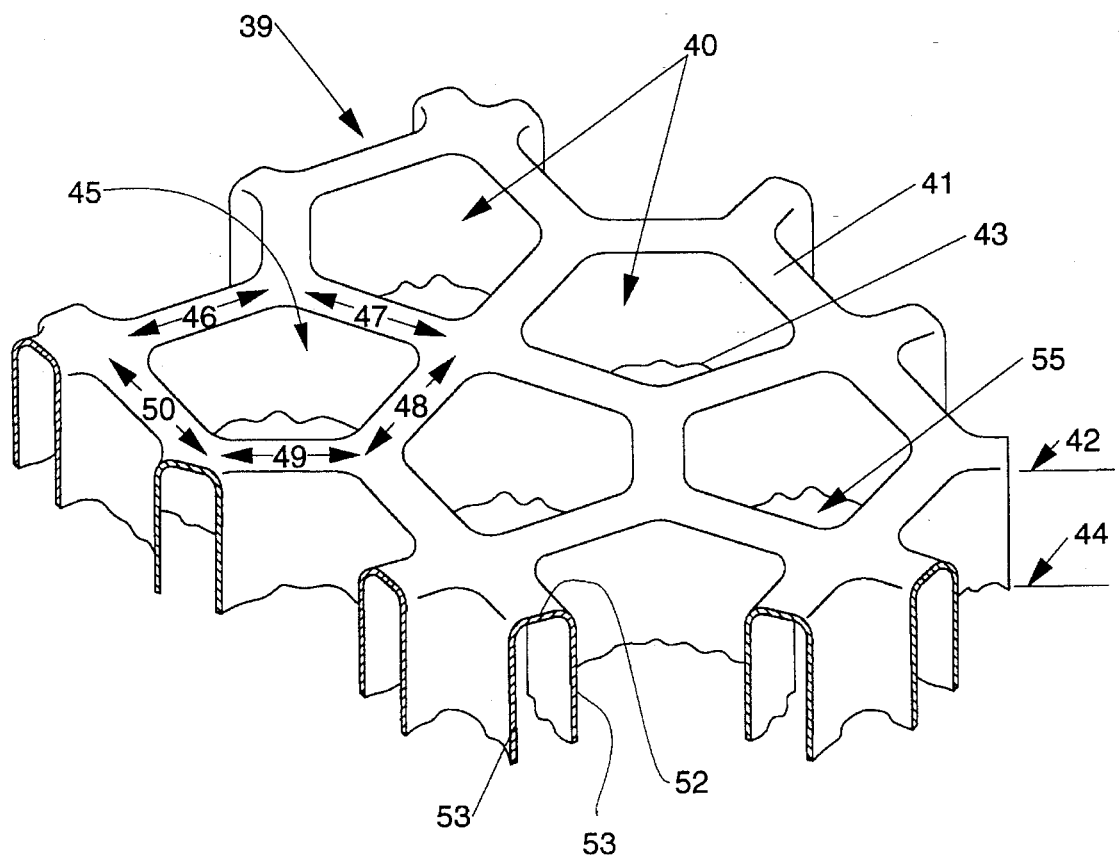
FIG. 3 is a greatly enlarged, segmented, perspective illustration of an apertured, three-dimensional, macroscopically expanded, formed film web of the type generally disclosed in commonly assigned U.S. Pat. No. 4,342,314, issued to Radel et al. which is suitable for use as the masking member.

FIG. 3 is an enlarged, partially segmented, perspective illustration of a preferred embodiment of an apertured, macroscopically expanded, three-dimensional, fiber-like, fluid pervious, plastic web 39 which has been found suitable for use as a masking member 29 on sanitary napkin 20. The term "macroscopically expanded", when used to describe three-dimensional plastic webs of the present invention, refers to webs, ribbons, and films which have been caused to conform to the surface of a three-dimensional forming structure so that both surfaces thereof exhibit a three-dimensional pattern of surface aberrations corresponding to the macroscopic cross-section of said forming structure, the surface aberrations comprising said pattern being individually discernible to the normal naked eye, i.e., a normal naked eye having 20/20 vision unaided by an instrument that changes the appearance, size or distance of an object or otherwise alters the visual powers of the eye, when the perpendicular distance between the viewer's eye and the plane of the web is about 12 inches. The term "fiber-like", as utilized herein to describe the appearance of plastic webs of the present invention, refers generally to any fine scale pattern of apertures, random or non-random, reticulated or non-reticulated, which connote an overall appearance and impression of a woven or nonwoven fibrous web when viewed by the human eye. As can be seen in FIG. 3, the web's fiber-like appearance is comprised of a continuum of fiber-like elements, the opposed ends of each of the fiber-like elements are interconnected to at least one other of the fiber-like elements. In the embodiment disclosed in FIG. 3, the interconnected fiber-like elements form a pattern network of pentagonally shaped capillaries 40. The web 39, which exhibits a fiber-like appearance, embodies a three-dimensional microstructure extending from the web's uppermost or wearer-contacting surface 41 in plane 42 to its lowermost or absorbent pad-contacting surface 43 in plane 44 to promote rapid fluid transport from the uppermost surface 41 to the lowermost surface 43 of the web without lateral transmission of fluid between adjacent capillaries 40. As utilized herein, the term "microstructure" refers to a structure of such fine scale that its precise detail is readily perceived by the human eye only upon magnification by a microscope or other means well-known in the art.

Apertures 45 are formed by a multiplicity of intersecting fiber-like elements, e.g., elements 46, 47, 48, 49, and 50, interconnected to one another in the first surface of the web. Each fiber-like element comprises a base portion, e.g., base portion 52, located in plane 42. Each base portion has a sidewall portion, e.g., sidewall portions 53, attached to each edge thereof. The sidewall portions 53 extend generally in the direction of the second surface 43 of the web. The intersecting sidewall portions of the fiber-like elements are interconnected to one another intermediate the first and second surface of the web and terminate substantially concurrently with one another in the plane 44 of the second surface.

In a particularly preferred embodiment, the interconnected sidewall portions terminate substantially concurrently with one another in the plane of the second surface 44 to form apertures 55 in the second surface 43 of the web. The network of capillaries 40 formed by the interconnected sidewall portions allows for free transfer of fluids from the first surface of the web directly to the second surface of the web without lateral transmission of fluid between adjacent capillaries.

Referring now to FIGS. 1 and 2, the masking member 29 defines a centrally disposed open area 60. As fluid impinges topsheet 24 it readily penetrates topsheet 24 and transfers into absorbent core 28. Fluid within absorbent core 28 then moves or wicks in the lateral and transverse directions towards the side and end edges, i.e., the periphery, of the absorbent core. As fluid approaches the side and end edges of the absorbent core, masking member 29 helps conceal the fluid contained within the side and end portions of the absorbent core. Furthermore, masking member 29 also helps to prevent side and end failure by providing an additional barrier to the escape of fluids along the side and end edges of the sanitary napkin 20.

Referring now to FIG. 2, masking member 29 is shown secured both to the topsheet 24 and the backsheet 26 to form a portion of the periphery 30. Alternatively, masking member 29 may be secured to the topsheet only, the backsheet only, or the absorbent core 28 only. The masking member may also be secured to any combination of the topsheet, backsheet or absorbent core. While masking member 29 is shown as a single piece of material, the masking member may be made of multiple pieces and be cut into a variety of shapes.

In use, the sanitary napkin 20 can be held in place by any support means or attachment means (not shown) well-known for such purposes. Preferably, the sanitary napkin is placed in the user's undergarment or panty and secured thereto by a fastener such as an adhesive. The adhesive provides a means for securing the sanitary napkin in the crotch portion of the panty. Thus, a portion or all of the outer surface 64 of the backsheet 26 is coated with adhesive. Any adhesive or glue used in the art for such purposes can be used for the adhesive herein, with pressure-sensitive adhesives being preferred. Suitable adhesives are Century A-305-IV manufactured by the Century Adhesives Corporation of Columbus, Ohio; and Instant Lock 34-2823 manufactured by the National Starch and Chemical Company of Bridgewater, N.J. Suitable adhesive fasteners are also described in U.S. Pat. No. 4,917,697. Before the sanitary napkin is placed in use, the pressure-sensitive adhesive is typically covered with a removable release liner in order to keep the adhesive from drying out or adhering to a surface other than the crotch portion of the panty prior to use. Suitable release liners are also described in the above-referenced U.S. Pat. No. 4,917,697. Any commercially available release liners commonly used for such purposes can be utilized herein. Non-limiting examples of suitable release liners are BL30MG-A Silox E1/0 and BL30MG-A Silox 4P/O both of which are manufactured by the Akrosil Corporation of Menasha, Wis. The sanitary napkin 20 of the present invention is used by removing the release liner and thereafter placing the sanitary napkin in a panty so that the adhesive contacts the panty. The adhesive maintains the sanitary napkin in its position within the panty during use.

In a preferred embodiment of the present invention, the sanitary napkin has two flaps each of which are adjacent to and extend laterally from the side edge of the absorbent core. The flaps are configured to drape over the edges of the wearer's panties in the crotch region so that the flaps are disposed between the edges of the wearer's panties and the thighs. The flaps serve at least two purposes. First, the flaps help serve to prevent soiling of the wearer's body and panties by menstrual fluid, preferably by forming a double wall barrier along the edges of the panty. Second, the flaps are preferably provided with attachment means on their garment surface so that the flaps can be folded back under the panty and attached to the garment facing side of the panty. In this way, the flaps serve to keep the sanitary napkin properly positioned in the panty. The flaps can be constructed of various materials including materials similar to the topsheet, backsheet, tissue, or combination of these materials. Further, the flaps may be a separate element attached to the main body of the napkin or can comprise extensions of the topsheet, masking member, and backsheet (i.e., unitary). A number of sanitary napkins having flaps suitable or adaptable for use with the sanitary napkins of the present invention are disclosed in U.S. Pat. No. 4,687,478, issued to Van Tilburg on Aug. 18, 1987; U.S. Pat. No. 4,589,876, issued to Van Tilburg on May 20, 1986; and U.S. Pat. No. 4,608,047, issued to Mattingly on Aug. 26, 1986. Each of these patents are incorporated herein by reference.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A sanitary napkin having a periphery, said sanitary napkin comprising:

(a) a fluid pervious topsheet;

(b) a fluid impervious backsheet joined to said topsheet;

(c) an absorbent core having a periphery positioned between said topsheet and said backsheet; and (d) a fluid pervious apertured formed film masking member positioned between said topsheet and said absorbent core, said masking member being disposed along the periphery of said sanitary napkin and covering the periphery of said absorbent core, said masking member thus defining a centrally disposed open area.

2. A sanitary napkin of claim 1, wherein said topsheet, said backsheet, and said masking member are secured together along their common periphery.

3. The sanitary napkin of claim 1, wherein said topsheet is an apertured formed film.

4. The sanitary napkin of claim 1, wherein said topsheet is a nonwoven material.

5. A sanitary napkin having a periphery, said sanitary napkin comprising:

(a) an apertured formed film topsheet;

(b) a fluid impervious backsheet joined to said topsheet;

(c) an absorbent core having a periphery positioned between said topsheet and said backsheet; and (d) a fluid pervious apertured formed film masking member positioned between said topsheet and said absorbent core, said masking member being disposed along the periphery of said sanitary napkin and covering the periphery of said absorbent core, said masking member thus defining a centrally disposed open area.

6. The sanitary napkin of claim 5, wherein said topsheet, said backsheet, and said masking member are secured together along their common periphery.

* * * * *